(12) United States Patent
Hoernig

(10) Patent No.: US 10,507,000 B2
(45) Date of Patent: Dec. 17, 2019

(54) METHOD FOR SIMULTANEOUS IMAGING OF FUNCTIONAL AND MORPHOLOGICAL X-RAY IMAGE DATA OF A BREAST, DIAGNOSTIC STATION, COMPUTER PROGRAM PRODUCT AND COMPUTER-READABLE MEDIUM

(71) Applicant: SIEMENS HEALTHCARE GMBH, Erlangen (DE)

(72) Inventor: Mathias Hoernig, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 177 days.

(21) Appl. No.: 15/697,638

(22) Filed: Sep. 7, 2017

(65) Prior Publication Data
US 2018/0078230 A1    Mar. 22, 2018

(30) Foreign Application Priority Data
Sep. 16, 2016    (DE) .................. 10 2016 217 776

(51) Int. Cl.
*A61B 6/00* (2006.01)
*A61B 6/02* (2006.01)

(52) U.S. Cl.
CPC .............. *A61B 6/502* (2013.01); *A61B 6/025* (2013.01); *A61B 6/463* (2013.01); *A61B 6/466* (2013.01); *A61B 6/469* (2013.01); *A61B 6/481* (2013.01); *A61B 6/482* (2013.01); *A61B 6/5235* (2013.01)

(58) Field of Classification Search
CPC ....... A61B 6/502; A61B 6/5235; A61B 6/481; A61B 6/469; A61B 6/463; A61B 6/482; A61B 6/025; A61B 6/466
See application file for complete search history.

(56) References Cited

U.S. PATENT DOCUMENTS

| | | | |
|---|---|---|---|
| 8,705,690 | B2 | 4/2014 | Jerebko et al. |
| 8,958,527 | B2 | 2/2015 | Muller et al. |
| 2003/0153830 | A1 | 8/2003 | Weinberg et al. |
| 2008/0130979 | A1* | 6/2008 | Ren .................. G06T 3/0006 382/132 |

(Continued)

FOREIGN PATENT DOCUMENTS

| | | |
|---|---|---|
| DE | 102011003137 A1 | 7/2012 |
| DE | 102012101142 A1 | 8/2012 |

*Primary Examiner* — Michael C Bryant
(74) *Attorney, Agent, or Firm* — Laurence Greenberg; Werner Stemer; Ralph Locher

(57) ABSTRACT

A method for simultaneous imaging of functional and morphological image data of a breast includes acquiring functional X-ray image data from the breast of a patient. In addition, morphological X-ray image data is acquired from the breast of the patient in the same breast position and with the same breast compression. A region of interest is defined on the basis of one of the two acquired data sets. A position of the region of interest is then determined in the other of the two acquired X-ray image data sets. The functional X-ray image data and the morphological X-ray image data are then each simultaneously graphically represented with the region of interest as a marked region. A diagnostic station, a non-transitory computer program product and a non-transitory computer-readable medium are also provided.

15 Claims, 3 Drawing Sheets

(56) References Cited

U.S. PATENT DOCUMENTS

| | | | |
|---|---|---|---|
| 2014/0072096 A1* | 3/2014 | Hoernig ................. | A61B 6/025 378/5 |
| 2016/0007943 A1* | 1/2016 | Hoernig ................. | A61B 6/482 378/37 |
| 2017/0065241 A1* | 3/2017 | Hoernig ................. | A61B 6/025 |

* cited by examiner

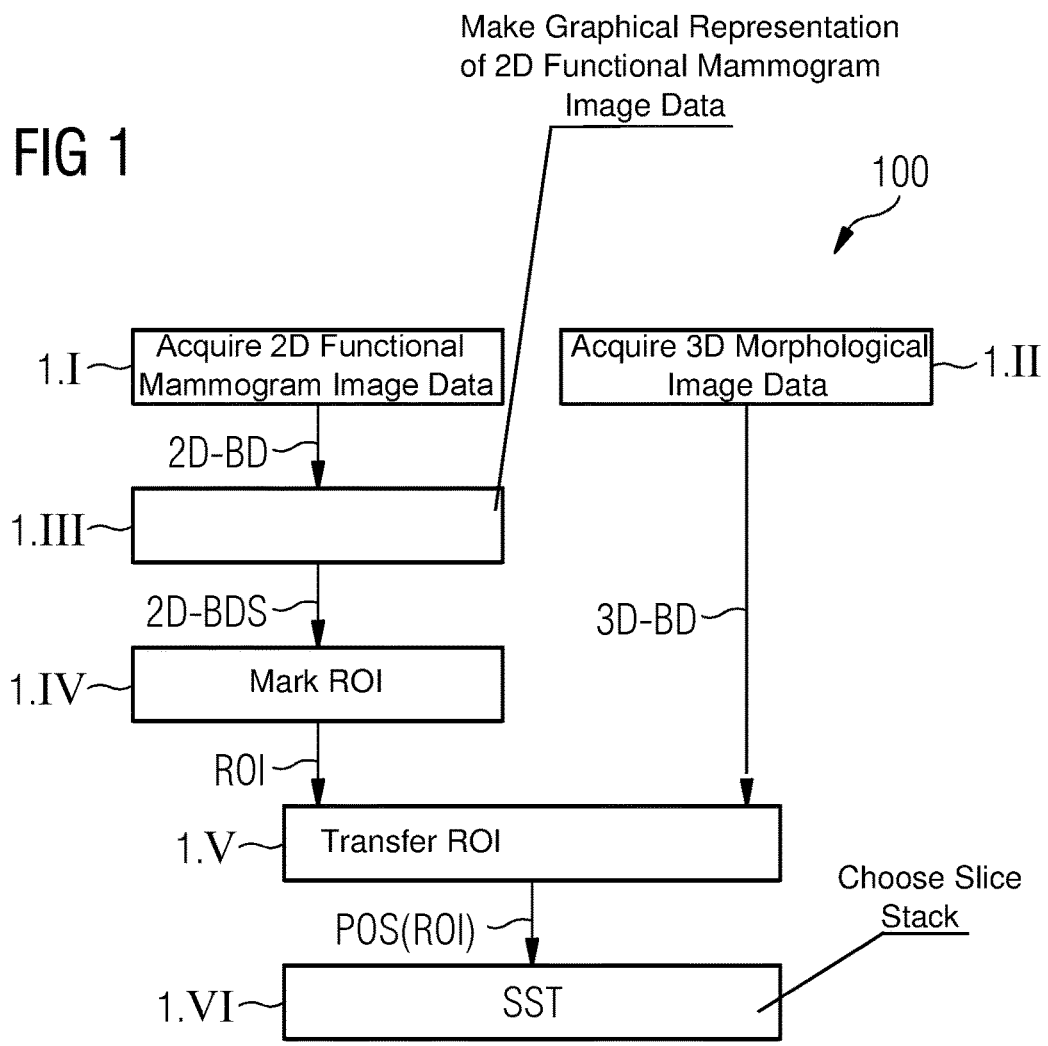

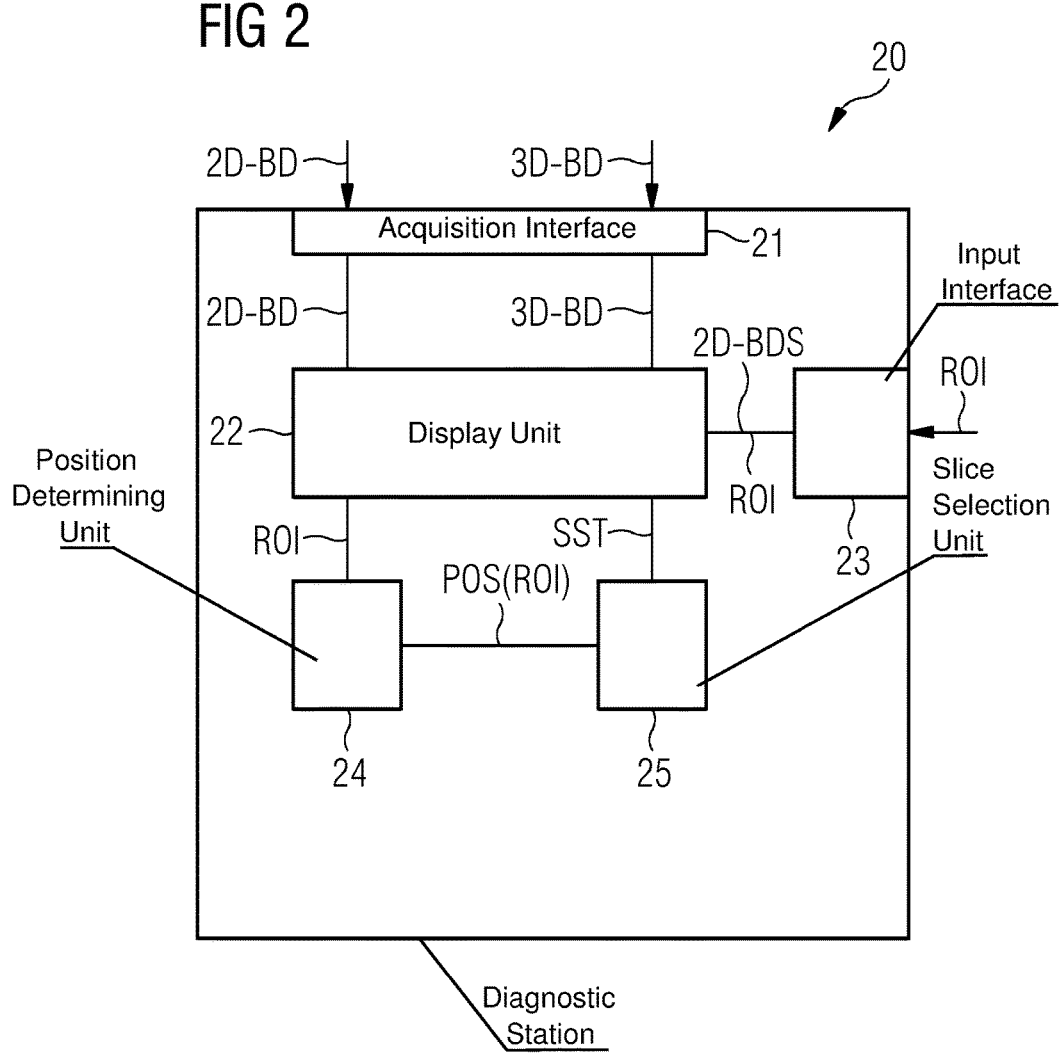

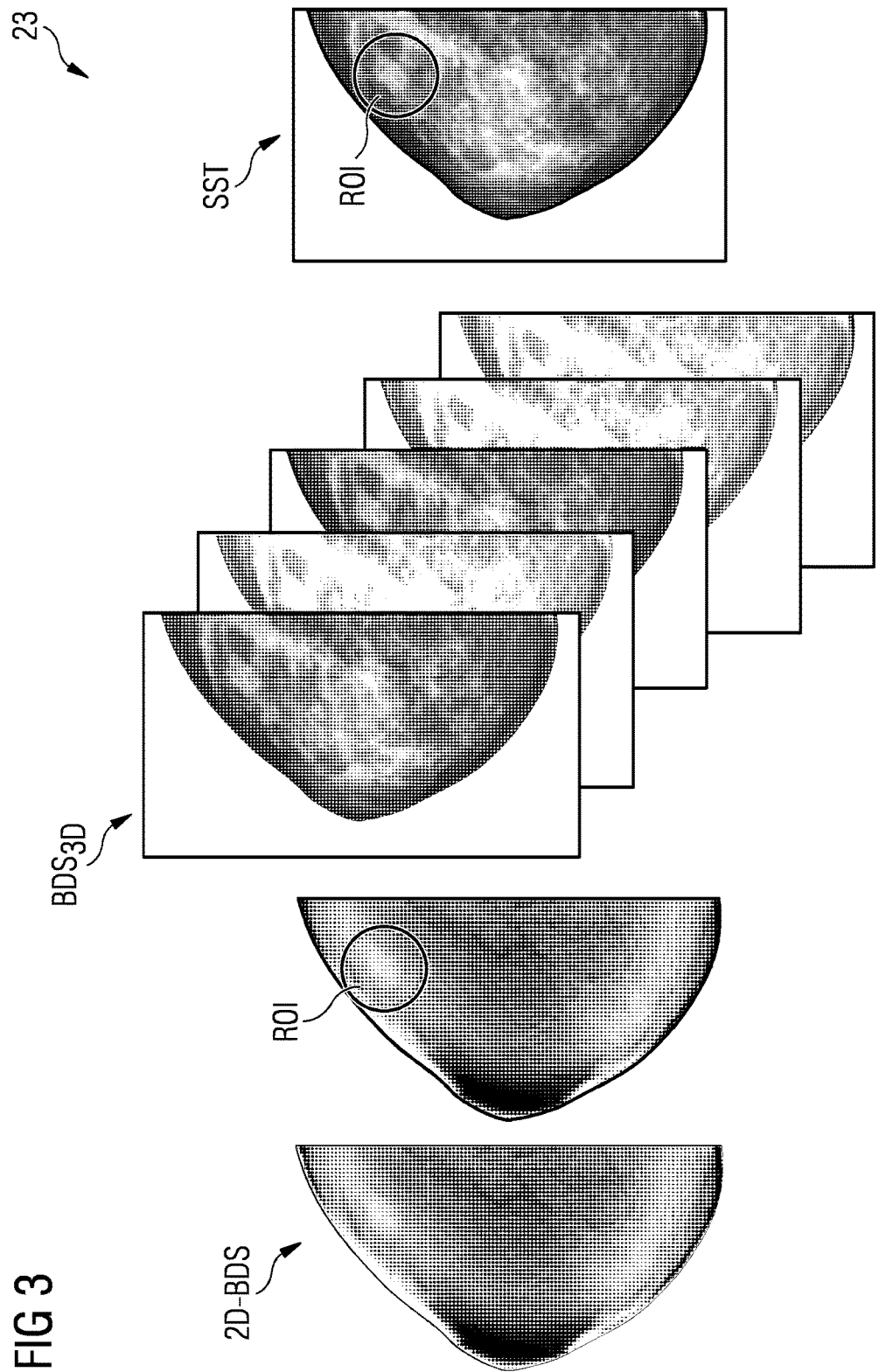

METHOD FOR SIMULTANEOUS IMAGING OF FUNCTIONAL AND MORPHOLOGICAL X-RAY IMAGE DATA OF A BREAST, DIAGNOSTIC STATION, COMPUTER PROGRAM PRODUCT AND COMPUTER-READABLE MEDIUM

CROSS-REFERENCE TO RELATED APPLICATION

This application claims the benefit, under 35 U.S.C. § 119, of German Patent Application DE 10 2016 217 776.1, filed Sep. 16, 2016; the prior application is herewith incorporated by reference in its entirety.

BACKGROUND OF THE INVENTION

Field of the Invention

The invention relates to a method for simultaneous imaging of functional and morphological X-ray image data of a breast. The invention relates, moreover, to a diagnostic station, a non-transitory computer program product and a non-transitory computer-readable medium.

For years mammography has been established as an imaging method in the framework of check-ups and for further diagnosis of breast carcinomas. In that case the breast is normally compressed and held in a fixed position while mammograms, usually single projection images, of the breast are generated by using X-ray radiation.

In mammography, X-ray imaging, tomosynthesis image recordings of the breast and their three-dimensional reconstructions thereof to form slice images are prior art diagnostic methods, while two-dimensional mammograms are primarily used for monitoring processes and as comparison images with previous images. (Digital) tomosynthesis is understood to mean a combination of digital image capture and processing with a slight movement of the X-ray source. Tomosynthesis has similarities to computer tomography (CT), but is regarded as a separate technique. Whereas in computer tomography, projection images are created during a complete 360° rotation of the X-ray source around the examination object, in tomosynthesis the X-ray source pivots only around a small angle of, for example 40°, with only a small number of projection images (typically between 7 and 60) being created. By using high-resolution detectors, a very high resolution can be achieved in planes perpendicular to the so-called Z-axis (axis in the direction of the tomosynthesis angle 0° or vertical direction from the X-ray source to the detector or orientation CC (Cranial-Caudal=from the head to the feet) even if the resolution is lower in the direction of the Z-axis. As compared to mammography, tomosynthesis works with a lower dose of radiation per projection.

Contrast Enhanced Dual Energy Mammography (abbreviated as CEDEM) is a relatively new diagnostic method. In that case two-dimensional low-energy images and two-dimensional high-energy images are respectively recorded with the passage of contrast medium and are then subtracted from each other to render the concentration of the contrast medium visible.

The three-dimensional position of a lesion can be determined very easily in the tomosynthesis recordings. By contrast, individual lesions can be located more easily in a CEDEM recording due to the stronger contrast.

If image recordings are created using both of those techniques, then during diagnosis it can therefore be advantageous for the radiologist to be able to evaluate a tomosynthesis recoding and a CEDEM recording simultaneously.

One problem with simultaneous evaluation lies in locating a region localized in one of the two graphical representations in the second graphical representation.

SUMMARY OF THE INVENTION

It is accordingly an object of the invention to provide a method for simultaneous imaging of functional and morphological X-ray image data of a breast, a diagnostic station, a computer program product and a computer-readable medium, which overcome the hereinafore-mentioned disadvantages of the heretofore-known methods and devices of this general type, which permit a simultaneous display of mammograms of diverse types and which enable linking in certain regions of the data of examined image recordings.

With the foregoing and other objects in view there is provided, in accordance with the invention, a method for simultaneous imaging of functional and morphological X-ray image data of a breast, including the following steps:
  acquiring functional X-ray image data, which includes
    two-dimensional mammogram image data, from the
    breast of a patient;
  acquiring morphological X-ray image data, which
    includes three-dimensional image data, from the breast
    of the patient in the same breast position and the same
    breast compression;
  defining a region of interest on the basis of one of the two
    acquired data sets;
  determining a position of the region of interest in the
    second of the two acquired X-ray image data sets; and
  simultaneous graphical representation of the functional
    X-ray image data and the morphological X-ray image
    data each with the region of interest as the marked
    region.

With the objects of the invention in view, there is also provided a diagnostic station, including:
  an acquisition interface for acquiring functional X-ray
    image data, which includes two-dimensional mammogram image data, from the breast of a patient, and for
    acquiring morphological X-ray image data, which
    includes three-dimensional image data, from the breast
    of the patient in the same breast position and the same
    breast compression;
  an input interface for determining a region of interest in
    one of the two acquired X-ray image data sets;
  a position-determining unit for determining a position of
    the region of interest in the second of the two acquired
    X-ray image data sets; and
  an image display unit for simultaneous graphical representation of the functional X-ray image data and the
    morphological X-ray image data each with the region
    of interest as the marked region.

With the inventive method for simultaneous imaging of functional and morphological X-ray image data of a breast, functional X-ray image data is acquired from the breast of a patient.

Within the scope of the present invention, the acquisition of X-ray image data should, as is conventional, be understood to mean an acquisition of imaging data for a diagnostic recording of, in particular, a compressed breast held in a specific position. This is conventionally projection data which can either be used directly as 2D-image data or can be processed further, for example, in order to obtain three-dimensional image data. Functional X-ray image data should be understood as X-ray image data which includes functional information. This is used, for example, as an indicator of an angiogenesis in the breast to be examined. In other words, the imaging of blood vessels, which point to the occurrence of lesions, is displayed by the functional information.

In addition, morphological X-ray image data is acquired from the breast of the patient in the same breast position and with the same breast compression as the functional X-ray image data. In this context, morphological X-ray image data should be understood to mean X-ray image data which makes clear structures of the breast and forms of the structures to be examined. Furthermore, a region of interest is defined on the basis of one of the two acquired X-ray image data sets. This process can occur, for example, by receiving an appropriate item of information about a region of interest, which information is transmitted by a user. For example, the user marks the position and the dimensions of the region of interest in a graphical representation of one of the two X-ray image data sets on a display. A position of the region of interest is then determined in the second of the two acquired X-ray image data sets. Finally, the functional X-ray image data and the morphological X-ray image data are each simultaneously depicted with the region of interest as the marked region.

Locating and linking or associating the region of interest in the two different X-ray image data sets is advantageously automated, so that the user is saved the time and effort required for manually locating the region of interest previously defined in one of the two image data sets. A diagnosis can therefore be made more quickly, reliably and conveniently.

A method, with which a region of interest can be transferred from one graphical representation of a breast into a second graphical representation of the breast, is described in more detail, for example, in German Patent Application DE 10 2011 003 137 A1, corresponding to U.S. Pat. No. 8,705,690, to which reference is hereby made and which is incorporated herein. Through the use of the method described therein a radiologist can mark a region in a first visualization and this is displayed by using a second visualization.

The inventive diagnostic station has an acquisition interface. The acquisition interface is used to acquire functional X-ray image data from the breast of a patient and to acquire morphological X-ray image data from the breast of the patient. The inventive diagnostic station also includes an input interface for determining a region of interest in one of the two acquired X-ray image data sets. At the input interface, for example a user interface of a screen, the user can choose in graphical representation of one of the two X-ray image data sets a region of interest which is then automatically transferred into the second of the two X-ray image data sets of the breast of the patient.

For a person making the diagnosis it can be easier to find and identify regions of interest using a graphical representation of one of the two X-ray image data sets. In addition, it is also important for the person making the diagnosis to obtain information about the regions of interest from the second of the two X-ray image data sets in order to be able to make a diagnosis.

For this purpose, the inventive diagnostic station includes a position-determining unit for determining a position of the region of interest in the second of the two acquired X-ray image data sets. Using the position-determining unit, a region of interest is—descriptively speaking—automatically transferred to the second of the two X-ray image data sets, so that the person making the diagnosis can immediately find and examine the structures associated with a region to be diagnosed in the second of the two X-ray image data sets without laborious searching. The inventive diagnostic station also includes an image display unit for simultaneous graphical representation of the functional X-ray image data and the morphological X-ray image data each with the region of interest as the marked region. On the basis of the marking of the region of interest in the two graphical representations, the person making the diagnosis can switch between the two graphical representations in order to combine the functional and morphological items of image information present therein with each other.

Some fundamental components of the inventive diagnostic station can be constructed for the most part in the form of software components. This relates, in particular, to the position-determining unit. Basically, these components can, however, also be partly implemented, in particular when especially fast calculations are involved, in the form of software-assisted hardware, for example FPGAs or the like. The required interfaces can likewise be constructed, for example when it is merely a matter of acquiring data from other software components, as software interfaces. They can, however, also be constructed as interfaces constructed in terms of hardware, which are controlled by appropriate software.

An implementation largely in terms of software has the advantage that even previously used diagnostic stations can be easily upgraded by way of a software update in order to work according to the invention. In this respect, the object of the invention is also achieved by a corresponding computer program product having a computer program which can be loaded directly into a storage device of a diagnostic station, having program segments to carry out all steps of the inventive method when the program is run in the diagnostic station. In addition to the computer program, a computer program product of this kind can optionally include additional components, such as, e.g. documentation and/or additional components, as well as hardware components, such as, e.g. hardware keys (dongles, etc.), for use of the software.

A computer-readable medium, for example, a memory stick, a hard disk or another transportable or permanently installed data carrier, on which the program segments of the computer program that can be read and executed by an arithmetic unit of the diagnostic station are stored, can be used for transport to the diagnostic station and/or for storing on or in the diagnostic station. For this purpose, the arithmetic unit can have, e.g., one or more collaborating microprocessor(s) or the like.

Further, particularly advantageous embodiments and developments of the invention result from the dependent claims and the following description, wherein the independent claims of one claim category can also be developed analogously to the dependent claims of a different claim category and, in particular, individual features of different exemplary embodiments or variants can also be combined to form new exemplary embodiments or variants.

In one embodiment of the inventive method the functional X-ray image data includes two-dimensional mammogram image data. The functional graphical representation is accordingly implemented in the form of a two-dimensional graphical representation. By contrast, the morphological X-ray image data in this embodiment includes three-dimensional image data, and the corresponding morphological graphical representation is implemented as a three-dimensional graphical representation.

If a person making the diagnosis has marked a two-dimensional region as the region of interest in the two-dimensional graphical representation with this variant, a three-dimensional position of the region of interest is then automatically determined in the three-dimensional morphological X-ray image data. Since the functional X-ray image data is present only as two-dimensional image data with this variant, initially the position and the dimensions of the region of interest is known only in two dimensions. In order to determine the third dimension of the dimensions and the position of the region of interest, first of all a region corresponding to the region of interest must be determined in the three-dimensional X-ray image data.

The region of interest is preferably defined in the functional two-dimensional graphical representation since it is easier to locate lesions there. In this case a three-dimensional position of the region of interest is then determined in the morphological three-dimensional X-ray image data. A slice stack encompassing the region of interest is then chosen in the morphological three-dimensional X-ray image data and graphically represented.

If the functional X-ray image data, as in this embodiment, exists as two-dimensional image data, initially the position and the dimensions of the region of interest are known in only two dimensions. In order to determine the third dimension of the dimensions and the position of the region of interest, first of all a region corresponding to the region of interest must be determined in the three-dimensional morphological X-ray image data. This can occur by using the method already mentioned in German Patent Application DE 10 2011 003 137 A1, corresponding to U.S. Pat. No. 8,705,690.

If the functional X-ray image data likewise exists as three-dimensional image data, the region of interest can in this case likewise be marked in the functional X-ray image data in three dimensions. The region of interest is then automatically transferred to the morphological X-ray image data since the position and extent of the region of interest are automatically determined in the functional X-ray image data and automatically transferred into the three-dimensional X-ray image data with morphological information.

Since the region of interest conventionally includes a distinctive structure, for the case where two-dimensional functional X-ray image data exists, the dimensions of the region of interest can be inferred in the third dimension by using the dimensions of the structure in the three-dimensional X-ray image data, so that the dimensions of the region of interest can also be determined in this case and be transferred to the morphological X-ray image data. Finally, a slice stack of the three-dimensional X-ray image data encompassing the region of interest is chosen. The three-dimensional morphological X-ray image data is conventionally divided into slices having uniform thickness and which can be individually displayed for the user. Depending on the extent of the region of interest, this can accordingly include one or more slice(s) which are combined into a single slice stack. In this context, a slice stack should therefore also be understood to mean the boundary case of just a single slice. The slice stack can then be illustrated for the user for example by displaying the individual slices. The three-dimensional slice-wise display of the region of interest provides the user with morphological information which cannot be seen in the functional graphical representation.

Since the blood vessels shown in the functional graphical representation are an indication of the possible occurrence of tumors, for a person making the diagnosis it is much easier to find or identify regions of interest using the functional graphical representation. In addition, however, it is also important for the person making the diagnosis to receive morphological information about the regions of interest in order to be able to form a diagnosis.

Alternatively, the region of interest can also be defined in the morphological graphical representation and a two-dimensional position of the region of interest can be determined in a data set encompassed by the functional two-dimensional X-ray image data. If, for example, striking structures are seen in the morphological image data, it can be useful to also examine the corresponding location in the functional image data.

Since the region of interest conventionally includes a distinctive structure, for the case where two-dimensional functional X-ray image data and three-dimensional morphological X-ray image data exist, the dimensions of the region of interest can be inferred in the third dimension using the dimensions of the structure in the three-dimensional X-ray image data, so that the dimensions of the region of interest can also be determined in this case and be transferred to the morphological X-ray image data.

Alternatively, the functional X-ray image data can also include three-dimensional X-ray image data which has been obtained on the basis of two three-dimensional image data sets using X-rays with different energies, i.e. different energy spectra. In this case the position and the extent of the region of interest can be determined directly by using the corresponding data of the functional graphical representation and be transferred to the second X-ray image data set respectively.

In one embodiment of the inventive method the functional X-ray image data includes contrast-enhanced image data. The contrast enhancement is achieved by injecting a contrast medium into the imaging region before image recording. The structures supplied with contrast medium can be rendered more easily visible with the aid of the contrast medium. For example, blood vessels in the breast tissue, which occur in connection with lesions, are rendered more easily visible thereby.

In one variant of the inventive method the two-dimensional functional image data includes dual-energy mammogram image data. With dual-energy imaging two image recordings are generated by using X-ray radiation having different energies. Background structures can be hidden by skillful weighted addition or subtraction of the two image recordings, so that the structures to be examined are rendered more easily visible. Images can also be generated by way of dual-energy image recordings so as to be differentiated according to materials. In a particularly practicable variant of the inventive method the two-dimensional functional image data can include, for example, a recombined image with iodine enrichment. This means that one of the two image recordings was generated by using a different energy by adding a contrast medium and the two image recordings were then recombined, i.e. the background of the contrasted structures was eliminated by subtraction of the two images.

In one advantageous variant of the inventive method the three-dimensional X-ray image data includes three-dimensional tomosynthesis image data. The tomosynthesis generates a series of thin slices throughout the breast. As a result, structures without overlays can be clearly worked out. In particular, in the case of dense glandular tissue, nodes or structures contained therein are difficult to see in the normal mammography summation recording. In this case tomosynthesis can be a clear advantage since individual slices can be examined separately. Tomosynthesis is suitable as a relatively low-radiation type of three-dimensional imaging of the breast for routine examinations.

In one embodiment of the inventive method the functional X-ray image data includes two data sets of three-dimensional tomosynthesis image data. The two data sets can include, for example, image data which was recorded by using different X-ray energies. Like dual-energy mammography, functional X-ray image data can also be generated with the aid of dual-energy three-dimensional imaging.

In addition to determining a three-dimensional position of the region of interest in the three-dimensional X-ray image data, the three-dimensional extent of the region of interest is preferably also determined with the inventive method. The three-dimensional extent of the region of interest can be determined, for example, by using the three-dimensional extent of the structures located in the region of interest. Determining the extent of the region of interest is important in order to determine which slices of the three-dimensional representation are encompassed by the region of interest.

For this purpose, in one variant of the inventive method the slices of the three-dimensional image data encompassed by the slice stack are defined as a function of the three-dimensional extent of the region of interest. This ensures that the user is shown the entire region of interest, defined first of all in the two-dimensional representation, slice-by-slice in three dimensions.

In one embodiment of the inventive method the chosen slice stack is displayed at the same time as the two-dimensional contrast medium-assisted graphical representation.

The functional and morphological data from the region of interest is advantageously displayed side by side for the user, so that he or she can easily combine the different items of information and gain an overall picture of the situation.

Typically, the slices of the morphological three-dimensional image data have a thickness of 1 mm. For the described simultaneous display, a 3D reconstruction of the morphological X-ray image data with thicker slices can also be purposefully provided or, alternatively, a plurality of slices can be joined to improve the accuracy of the linking of the region of interest in the functional graphical representation to the three-dimensional morphological graphical representation.

In a specific embodiment of the inventive method a synthetic mammogram is calculated on the basis of the three-dimensional tomosynthesis image data when determining the three-dimensional position of the region of interest. A low-energy image is also generated on the basis of the two-dimensional dual-energy mammogram image data. The structures encompassed by the marked region are then compared with the structures of the synthetic mammogram.

The 3D tomosynthesis data set is a low/standard energy data set. The synthetic mammogram calculated therefrom therefore depicts the morphological structures in roughly the same image quality as a native low-energy mammogram. As is known from German Patent Application DE 10 2011 003 137 A1, corresponding to U.S. Pat. No. 8,705,690, a good correlation of regions of interest (ROIs) of a synthetic mammogram with the relevant tomosynthesis slice can be attained. By comparing the synthetic mammogram with the low-energy image by analogy, a comparable level of accuracy to the low-energy image can be achieved in the ROI association from a recombined image and the corresponding ROI association. Structures encompassed by the marked regions are subsequently localized and marked in the two-dimensional dual-energy mammogram image data and the region of interest is transferred to the synthetic mammogram or the low-energy image. Finally, the synthetic mammogram provided with the region of interest is back projected onto a three-dimensional tomosynthesis graphical representation.

In principle, it is also possible to use the high-energy image for the comparison since the high-energy image is recorded in the same position of the breast as the low-energy image. Due to the loss of contrast in the high-energy image (and the higher noise fraction due to the lower dose of the high-energy recording (typically 20-50% of the low-energy image)), morphological structures can be seen much more clearly in the low-energy image than in the high-energy image.

In the method according to the invention, the step of determining a three-dimensional position of the region of interest in the three-dimensional tomosynthesis image data is preferably carried out automatically. In this way, the user is released from a laborious search for the region of interest in the three-dimensional morphological image data, and this speeds up diagnosis and allows the user to direct his or her attention solely to making a diagnosis.

Other features which are considered as characteristic for the invention are set forth in the appended claims.

Although the invention is illustrated and described herein as embodied in a method for simultaneous imaging of functional and morphological X-ray image data of a breast, a diagnostic station, a computer program product and a computer-readable medium, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a flow diagram which illustrates a method for simultaneous imaging of functional and morphological X-ray image data of a breast;

FIG. 2 is a block diagram of a diagnostic station according to one exemplary embodiment of the invention; and FIG. 3 shows a simultaneous representation of two-dimensional mammograms and three-dimensional tomosynthesis images which are linked to each other.

DETAILED DESCRIPTION OF THE INVENTION

Referring now in detail to the figures of the drawings, in which identical components are provided with identical reference numerals and which, as a rule, are not to scale, and first, particularly, to FIG. 1 thereof, there is seen a flow diagram which illustrates a method for simultaneous imaging of functional and morphological image data of a breast according to one exemplary embodiment of the invention. In step 1.I two-dimensional functional mammogram image data 2D-BD is firstly acquired from a breast of a patient. In the exemplary embodiment shown in FIG. 1 functional mammogram image data 2D-BD is acquired in step 1.I using a contrast medium-assisted dual-energy imaging method in which so-called low-energy image data and high-energy image data is generated having a differential image which corresponds to a representation of the functional properties of a region to be imaged. For example, blood vessels can be seen particularly clearly, wherein a concentration of blood vessels in the breast tissue can be an indication of a lesion that needs to be examined more closely.

In step 1.II three-dimensional morphological image data 3D-BD is acquired from the breast of the patient within the framework of tomosynthesis image recording. This takes place with the same compression as the acquisition of the two-dimensional functional image data.

In step 1.III a graphical representation 2D-BDS is made of the two-dimensional functional mammogram image data 2D-BD on an interactive image display of a diagnostic station. In step 1.IV a region of interest ROI is then marked in the two-dimensional graphical representation 2D-BDS by a radiologist, which is a region that is to be examined more closely in the three-dimensional image data 3D-BD. In step 1.V the region of interest ROI defined in the two-dimensional graphical representation 2D-BDS is then transferred to the three-dimensional image data 3D-BD, i.e. the position POS(ROI) and the extent of the region of interest ROI are determined in the three-dimensional image data 3D-BD. For this process, a two-dimensional synthetic mammogram can be generated, for example on the basis of the three-dimensional image data 3D-BD, by way of forward projection. The two-dimensional synthetic mammogram is then compared with the low-energy image of the functional two-dimensional image data 2D-BD. The region of interest ROI is transferred herein to the two-dimensional synthetic mammogram. This means that the position of the region of interest ROI is determined in the two-dimensional synthetic mammogram (see also German Patent Application DE 10 2011 003 137 A1, corresponding to U.S. Pat. No. 8,705,690).

After marking the region of interest ROI in the two-dimensional synthetic mammogram, the two-dimensional synthetic mammogram with the marked region ROI is back-projected into the three-dimensional space. This then produces the position and extent of the region of interest ROI in the three-dimensional graphical representation. Finally, in step 1.VI a slice stack SST of the three-dimensional image data 3D-BD encompassing the region of interest ROI is chosen. This occurs automatically as a function of the position and extent of the region of interest ROI. The slices of the slice stack SST are then displayed individually or combined on the image display, so that a radiologist can examine them.

FIG. 2 shows a block diagram of a diagnostic station 20 according to one exemplary embodiment of the invention. The diagnostic station 20 includes an acquisition interface 21. The acquisition interface 21 is used to receive two-dimensional functional mammogram image data 2D-BD from the breast of a patient. The two-dimensional functional mammogram image data 2D-BD can be transmitted, for example, from a mammography unit or a database. Furthermore, three-dimensional image data 3D-BD is received from the breast of the patient with the aid of the acquisition interface 21. The three-dimensional image data 3D-BD can, for example, be tomosynthesis image data which is transmitted from a tomosynthesis device or a database to the diagnostic station 20. The acquired image data 2D-BD, 3D-BD is transmitted to an image display unit 22 which displays the image data 2D-BD, 3D-BD for a user.

The diagnostic station 20 then receives data from a user through an input interface 23 with respect to the position and extent of a region of interest ROI. The data with respect to the region of interest ROI can be input, for example, by the user marking that region in a functional two-dimensional representation 2D-BDS of the acquired functional image data 2D-BD. The region of interest ROI is firstly displayed in the functional two-dimensional graphical representation 2D-BDS on the display. In addition, the data relating to the region of interest ROI is transmitted to a position-determining unit 24. On the basis of the data relating to the region of interest ROI, the position-determining unit 24 determines a position POS(ROI) and an extent of this region in a three-dimensional morphological representation associated with the three-dimensional image data 3D-BD. This can occur, for example, in the manner described in connection with step 1.V. The diagnostic station 20 also includes a slice-selection unit 25 which determines a slice stack SST encompassing the region of interest ROI on the basis of the position POS(ROI) and extent of the region of interest ROI in the three-dimensional morphological representation. The determined slice stack SST is then displayed on the image display of the image display unit 22 at the same time as the two-dimensional mammogram image 2D-BDS.

FIG. 3 shows a simultaneous graphical representation of two-dimensional functional image data and three-dimensional image data of a breast of a patient on a touchscreen 23. A representation 2D-BDS of the two-dimensional functional image data 2D-BD is shown on the touchscreen 23 in a section on the left. The two-dimensional representation 2D-BDS with a recorded region of interest ROI can be seen on the right, next to the representation 2D-BDS of the two-dimensional functional image data 2D-BD. A middle image section shows the three-dimensional image data 3D-BD in a slice-by-slice, three-dimensional graphical representation $BDS_{3D}$. A representation of a chosen slice SST can be seen in an image section on the right, and this includes the region of interest ROI. Using the three-dimensional graphical representation $BDS_{3D}$ in addition to the functional features from the representation 2D-BDS of the functional image data 2D-BD, a user can accordingly still obtain morphological information with the aid of which a diagnosis of the breast being examined is easier and more reliable.

To conclude, reference is again made to the fact that the devices and methods described above in detail are merely exemplary embodiments which can be modified by a person skilled in the art in a wide variety of ways without departing from the scope of the invention. Furthermore, use of the indefinite article "a" or "an" does not preclude the relevant features from also being present multiple times. Similarly, the term "unit" does not preclude the relevant components from including several cooperating subcomponents which can optionally also be spatially distributed.

The following is a summary list of reference numerals and the corresponding structure used in the above description of the invention. List of reference numerals:
20 diagnostic station
21 acquisition interface
22 image display unit
23 input interface
24 position-determining unit
25 slice-selection unit
2D-BD two-dimensional functional mammogram image data
2D-BDS graphical representation of the two-dimensional functional mammogram image data
3D-BD three-dimensional image data
$BDS_{3D}$ three-dimensional graphical representation
POS(ROI) position of the region of interest
ROI region of interest
SST slice stack of the three-dimensional image data

The invention claimed is:

1. A method for simultaneous imaging of functional and morphological X-ray image data of a breast, the method comprising the following steps:
   acquiring a functional X-ray image data set including two-dimensional dual-energy mammogram image data, from the breast of a patient;
   acquiring a morphological X-ray image data set including three-dimensional image data, from the breast of the patient in the same breast position and with the same breast compression;
   determining a region of interest in the functional graphical representation;
   determining a three-dimensional position of the region of interest in the morphological three-dimensional X-ray image data;
   simultaneously graphically representing the functional X-ray image data and the morphological X-ray image data each with the region of interest as a marked region;
   choosing a slice stack, including the region of interest, of the morphological three-dimensional X-ray image data;
   graphically representing the chosen slice stack; and
   determining the three-dimensional position of the region of interest by performing following steps:
      calculating a synthetic mammogram on a basis of the three-dimensional tomosynthesis image data;
      generating a low-energy image on a basis of the two-dimensional dual-energy mammogram image data;
      comparing structures encompassed by the region of interest with structures of the synthetic mammogram;
      localizing and marking structures encompassed by the region of interest in the two-dimensional dual-energy mammogram image data;
      transferring the region of interest to the synthetic mammogram; and
      back-projecting the synthetic mammogram provided with the region of interest onto a three-dimensional tomosynthesis graphical representation.

2. The method according to claim 1, wherein:
   the graphical representation of the functional X-ray image data includes a two-dimensional graphical representation; and
   the graphical representation of the morphological X-ray image data includes a three-dimensional graphical representation.

3. The method according to claim 1, which further comprises:
   defining the region of interest in the morphological graphical representation; and
   determining a two-dimensional position of the region of interest in a data set encompassed by the functional two-dimensional X-ray image data.

4. The method according to claim 1, wherein the functional X-ray image data includes contrast-enhanced X-ray image data.

5. The method according to claim 1, wherein the functional X-ray image data includes dual-energy mammogram image data.

6. The method according to claim 1, wherein the morphological X-ray image data includes three-dimensional tomosynthesis image data.

7. The method according to claim 1, which further comprises determining a three-dimensional extent of the region of interest in addition to determining a three-dimensional position of the region of interest in the morphological three-dimensional X-ray image data.

8. The method according to claim 7, which further comprises determining slices of the three-dimensional X-ray image data encompassed by the slice stack as a function of the three-dimensional extent of the region of interest.

9. A non-transitory computer program product stored in a non-transitory storage device of a diagnostic station, the program product comprising:
   program segments for carrying out the steps of the method according to claim 1 when said computer program product is run in the diagnostic station.

10. A non-transitory computer-readable medium with program segments stored thereon, that when read and executed by an arithmetic unit, perform the steps of the method according to claim 1 when the program segments are run by the arithmetic unit.

11. A method for simultaneous imaging of functional and morphological X-ray image data of a breast, the method comprising the following steps:
   acquiring a functional X-ray image data set including two-dimensional mammogram image data, from the breast of a patient;
   acquiring a morphological X-ray image data set including three-dimensional image data, from the breast of the patient in the same breast position and with the same breast compression, the morphological X-ray image data including three-dimensional tomosynthesis image data;
   determining a region of interest in the functional graphical representation;
   determining a three-dimensional position of the region of interest in the morphological three-dimensional X-ray image data;
   simultaneously graphically representing the functional X-ray image data and the morphological X-ray image data each with the region of interest as a marked region;
   choosing a slice stack, including the region of interest, of the morphological three-dimensional X-ray image data;
   graphically representing the chosen slice stack; and
   carrying out the step of determining the three-dimensional position of the region of interest by performing following steps:
      calculating a synthetic mammogram on a basis of the three-dimensional tomosynthesis image data;
      generating a low-energy image on a basis of the two-dimensional dual-energy mammogram image data;
      comparing structures encompassed by the region of interest with the structures of the synthetic mammogram;
      localizing and marking structures encompassed by the region of interest in the two-dimensional dual-energy mammogram image data;
      transferring the region of interest to the synthetic mammogram; and
      back-projecting the synthetic mammogram provided with the region of interest onto a three-dimensional tomosynthesis graphical representation.

12. A method for simultaneous imaging of functional and morphological X-ray image data of a breast, the method comprising the following steps:
   acquiring a functional X-ray image data set including two-dimensional mammogram image data, from the breast of a patient;
   acquiring a morphological X-ray image data set including three-dimensional image data, from the breast of the patient in the same breast position and with the same breast compression;

determining a region of interest in the functional graphical representation;
determining a three-dimensional position of the region of interest in the morphological three-dimensional X-ray image data;
simultaneously graphically representing the functional X-ray image data and the morphological X-ray image data each with the region of interest as a marked region;
choosing a slice stack, including the region of interest, of the morphological three-dimensional X-ray image data;
graphically representing the chosen slice stack;
determining a three-dimensional extent of the region of interest in addition to determining a three-dimensional position of the region of interest in the morphological three-dimensional X-ray image data; and
carrying out the step of determining the three-dimensional position of the region of interest by performing following steps:
calculating a synthetic mammogram on a basis of the three-dimensional tomosynthesis image data;
generating a low-energy image on a basis of the two-dimensional dual-energy mammogram image data;
comparing structures encompassed by the region of interest with the structures of the synthetic mammogram;
localizing and marking structures encompassed by the region of interest in the two-dimensional dual-energy mammogram image data;
transferring the region of interest to the synthetic mammogram; and back-projecting the synthetic mammogram provided with the region of interest onto a three-dimensional tomosynthesis graphical representation.

13. A method for simultaneous imaging of functional and morphological X-ray image data of a breast, the method comprising the following steps:
acquiring a functional X-ray image data set including two-dimensional mammogram image data, from the breast of a patient;
acquiring a morphological X-ray image data set including three-dimensional image data, from the breast of the patient in the same breast position and with the same breast compression;
determining a region of interest in the functional graphical representation;
determining a three-dimensional position of the region of interest in the morphological three-dimensional X-ray image data;
simultaneously graphically representing the functional X-ray image data and the morphological X-ray image data each with the region of interest as a marked region;
choosing a slice stack, including the region of interest, of the morphological three-dimensional X-ray image data;
graphically representing the chosen slice stack;
determining slices of the three-dimensional X-ray image data encompassed by the slice stack as a function of the three-dimensional extent of the region of interest; and
carrying out the step of determining the three-dimensional position of the region of interest by performing following steps:
calculating a synthetic mammogram on a basis of the three-dimensional tomosynthesis image data;
generating a low-energy image on a basis of the two-dimensional dual-energy mammogram image data;
comparing structures encompassed by the region of interest with the structures of the synthetic mammogram;
localizing and marking structures encompassed by the region of interest in the two-dimensional dual-energy mammogram image data;
transferring the region of interest to the synthetic mammogram; and back-projecting the synthetic mammogram provided with the region of interest onto a three-dimensional tomosynthesis graphical representation.

14. The method according to claim 1, which further comprises automatically carrying out the step of determining a position of the region of interest.

15. A diagnostic station, comprising:
an acquisition interface for acquiring a functional X-ray image data set including two-dimensional mammogram image data, from the breast of a patient, and for acquiring a morphological X-ray image data set including three-dimensional image data from the breast of the patient in the same breast position and with the same breast compression;
an input interface for determining a region of interest in one of the two acquired X-ray image data sets;
a position-determining unit for determining a three-dimensional position of the region of interest in the other of the two acquired X-ray image data sets by:
calculating a synthetic mammogram on a basis of the three-dimensional tomosynthesis image data;
generating a low-energy image on a basis of the two-dimensional dual-energy mammogram image data;
comparing structures encompassed by the region of interest with structures of the synthetic mammogram;
localizing and marking structures encompassed by the region of interest in the two-dimensional dual-energy mammogram image data;
transferring the region of interest to the synthetic mammogram; and
back-projecting the synthetic mammogram provided with the region of interest onto a three-dimensional tomosynthesis graphical representation; and
an image display unit for simultaneous graphical representation of the functional X-ray image data and the morphological X-ray image data each with the region of interest as a marked region.

* * * * *